United States Patent [19]

Hanna et al.

[11] Patent Number: 4,657,757

[45] Date of Patent: Apr. 14, 1987

[54] CONTROLLED RELEASE DOSAGE FORM COMPRISING ACETAMINOPHEN, PSEUDOEPHEDRINE SULFATE AND DEXBROMPHENIRAMINE MALEATE

[75] Inventors: Gayda Hanna, Berwyn, Pa.; Winston A. Vadino, Bridgewater, N.J.

[73] Assignee: Schering Corporation, Kenilworth, N.J.

[21] Appl. No.: 804,707

[22] Filed: Dec. 4, 1985

Related U.S. Application Data

[63] Continuation-in-part of Ser. No. 718,036, Mar. 29, 1985, Pat. No. 4,601,894.

[51] Int. Cl.[4] .......................... A61K 9/22; A61K 9/26
[52] U.S. Cl. .................................... 424/488; 514/781
[58] Field of Search ................................ 424/14–22, 424/35; 514/781

[56] References Cited

U.S. PATENT DOCUMENTS 3,065,143 11/1962 Christenson et al. ................. 424/19
4,226,849 10/1980 Schor ................................. 514/781
4,259,314 3/1981 Lowey ............................... 514/781
4,369,172 1/1983 Schor et al. ........................ 514/781
4,389,393 6/1983 Schor et al. ........................ 514/781

OTHER PUBLICATIONS

A.Ph.A. Handbook of Non-Prescription Drugs 6th ED (1979), pp. 73–114 Cold and Allergy Products.
PDR 1984 38th ED. Physcians Desk Reference pp. 214, 215, 216, 301, 302, 305, 307, 309, 326, 327, 972, 973, 993, 1176, 1385, 1758, 1759, 1802, 1803.
Manford Robinson, Chapter 14, "Sustained Action Dosage Forms", *The Theory and Practice of Industrial Pharmacy*, 2nd ed., ed., ed., L. Lachman et al (1976).
"Formulating Sustained Release Pharmaceutical Products with Methocel", The Dow Chemical Co., 1982.

*Primary Examiner*—Shep K. Rose
*Attorney, Agent, or Firm*—Anita W. Magatti; Stephen I. Miller; James R. Nelson

[57] ABSTRACT

The invention relates to a controlled release dosage form comprising three actives: acetaminophen, pseudoephedrine sulfate and dexbrompheniramine maleate.

15 Claims, No Drawings

CONTROLLED RELEASE DOSAGE FORM COMPRISING ACETAMINOPHEN, PSEUDOEPHEDRINE SULFATE AND DEXBROMPHENIRAMINE MALEATE

This application is a continuation in-part of application Ser. No. 718,036, filed Mar. 29, 1985, now U.S. Pat. No. 4,601,894.

SUMMARY OF THE INVENTION

The present invention relates to an oral controlled release matrix dosage form which combines three pharmaceuticals, acetaminophen, pseudoephedrine or a pharmaceutically acceptable salt thereof and dexbrompheniramine or a pharmaceutically acceptable salt thereof, one or more polymers, and excipients.

BACKGROUND OF THE INVENTION

Acetaminophen is a well known analgesic and antipyretic which reduces the discomfort and fever due to colds and other viral infections.

Pseudoephedrine and pharmaceutically acceptable salts thereof, e.g. the sulfate and the hydrochloride, are well known decongestants which restore freer breathing by shrinking nasal passages and promote sinus drainage in those suffering from colds, allergies or sinusitis.

Dexbrompheniramine and pharmaceutically acceptable salts thereof, e.g. the maleate, are well known antihistamines which provide relief of the pruritis, rhinitis and sneezing associated with colds and allergies.

Controlled release dosage forms which comprise a single active component are well known, including matrix tablet systems incorporating active ingredients, lubricants, binders, fillers and other excipients, wherein the binders may be hydrophillic, hydrophobic or water insoluble polymers. See for example U.S. Pat. No. 4,389,393. However, controlled release dosage forms which combine two actives are not common, and no controlled release dosage forms combining three actives in a single uniform dosage form are known because of the difficulties encountered in combining multiple actives, each with different chemical and physical characteristics, different release rates, different half-lives and different dosage sizes.

The mechanism by which controlled release dosage forms act to dispense the active ingredients over a period of time have been described at length in the literature. See for example Manford Robinson, Chapter 14, "Sustained Action Dosage Forms", *The Theory and Practice of Industrial Pharmacy*, 2nd. ed., ed. L. Lachman, H. Lieberman and J. Kanig (Philadelphia; Lea & Febiger, 1976).

DETAILED DESCRIPTION OF THE INVENTION

The controlled release dosage form which is the subject of this invention represents a novel advancement of the art since it combines three active ingredients, acetaminophen, pseudoephedrine or a pharmaceutically acceptable salt thereof, preferably pseudoephedrine sulfate, and dexbrompheniramine or a pharmaceutically acceptable salt thereof, preferably dexbrompheniramine maleate, in a single long-acting tablet. While antihistamines and decongestants have been combined in controlled release tablets, and while antihistamines, decongestants and analgesics have been combined in 2-layer tablets or have been separately microencapsulated and combined in continuous action capsules, the present invention relates to a surprisingly simple combination of three actives in a single homogenous matrix, from which matrix each active component is released at an appropriate rate to provide the desired activity over a period of 2-14, preferably 8-12 hours.

The components of the matrix are preferably chosen so that a dosage form of the present invention releases the actives over a period of 12 hours.

It is most unexpected that each active component is released from the matrix at its desired rate despite the differences in solubilities among the actives in gastric or aqueous media, indicating that different mechanisms of drug release, i.e. diffusion through, and erosion of the hydrated layer, are occurring simultaneously. Another unexpected feature is that the differences in dosage size do not affect the appropriate release of each of the actives. That is, acetaminophen, pseudoephedrine and dexbrompheniramine may be present at an approximate weight ratio of 200:20:1, for example, and the desired sustained release rates for each are still obtained. It is also unexpected that three actives with significantly different biological half-lives should each demonstrate its own efficacious pharmacological profile when combined in a single sustained release dosage form.

The specific preferred combination of actives of the invention, i.e. acetaminophen, pseudoephedrine sulfate and dexbrompheniramine maleate, presents an advantage to cold and allergy sufferers by providing a single sustained release medicament with antihistaminic, decongestant and analgesic properties. Thus, repeated administration of several single component dosage forms throughout the day may be avoided. Moreover, it is apparent that in addition to the well known pharmacological advantages of a controlled release formulation in general (e.g. more constant blood levels of the drugs), the dosage form of the present invention is easier and more economical to manufacture than microencapsulated or multi-layered dosage forms.

Although the three actives and one or more polymers must always be present in the dosage form of the invention, the concentrations of the actives and polymer may vary. For the filler and other excipients, the nature as well as each concentration of the component may also vary.

Acetaminophen may be present at from 400 to 750 mg/tablet, preferably 500 mg/tablet. Pseudoephedrine sulfate may be present at from 15 to 75 mg/tablet, preferably 60 mg/tablet. Dexbrompheniramine maleate may be present in the range of 1 to 5 mg/tablet, with 3 mg/tablet being preferred.

While a number of polymers might be used as the binder for the matrix, this invention particularly contemplates the use of hydroxypropyl methylcellulose (HPMC) ethers or combinations of HPMC and methylcellulose, sodium carboxymethylcellulose, ethylcellulose, or other cellulose ethers. A single HPMC ether may be used, or a mixture of HPMC ethers of different molecular weight and structure may be used, e.g., HPMC ethers of the same structure and different molecular weight or HPMC ethers of different structure and the same molecular weight may be combined. Where HPMC is combined with another polymer, a combination of HPMC and ethylcellulose is preferred. A variety of HPMC ethers is commercially available, for example Dow's METHOCEL K, HPMC (USP 2208), METHOCEL E, HPMC (USP 2910), and METHOCEL F, HPMC (USP 2906). See "Formulating Sustained Release Pharmaceutical Products with Methocel" (The Dow Chemical Co., 1982). METHOCEL, METHOCEL K, METHOCEL E and METHOCEL F are all trademarks of the Dow Chemical Company.

Of the total polymer weight, 100-55% may be HPMC or a mixture of HPMC ethers and 0-45% may be ethylcellulose. For dual polymer systems, e.g. wherein 99-55% of the total polymer weight may be HPMC or a mixture of HPMC ethers and 1-45% may be ethylcellulose, preferred ranges of polymer weight are 66.5-55% HPMC and 33.5-45% ethylcellulose. When only HPMC or a mixture of HPMC ethers is used, the total polymer content represents 1-8% by weight of the dosage form (i.e., the uncoated core dosage form), and for a dual system the total polymer content represents 8-15% by weight of the dosage form. A preferred range for the total amount of polymer present for the single polymer system is 6-6.5% by weight of the dosage form, and for the dual polymer system, the preferred range is 11.5-12.5%. In a preferred embodiment, HPMC is the only polymer used, i.e. 100% HPMC, with 100% HPMC USP 2208 (e.g., HPMC K4M from The Dow Chemical Co., specified as having a methoxyl content of 19-24 weight-%, a hydroxypropyl content of 7-12 weight-%, a number average molecular weight of 89,000, and wherein the viscosity of a 2% aqueous solution is 3500-5600 cps) and 100% HPMC USP 2910 (e.g., HPMC E4M from The Dow Chemical Co., specified as having a methoxyl content of 28-30 weight-%, a hydroxypropyl content of 7-12 weight-%, a number average molecular weight of 93,000, and wherein the viscosity of 2% aqueous solution is 3500-5600 cps) being more preferred. Another preferred embodiment is a dual polymer system having a total polymer weight of 11.5-12.5 of the dosage form wherein the polymer system is comprised of about 55-60%, more preferably 58% HPMC and about 40-45%, more preferably 42% ethylcellulose.

Also present in the matrix are one or more fillers such as dibasic calcium phosphate dihydrate or lactose, with dibasic calcium phosphate dihydrate being preferred. The filler is present in an amount of 10-13% of the total dosage form weight, with about 12% being preferred.

When the weight of the polymer component is varied, corresponding variations in the filler weight are made in order to maintain constant tablet weight and controlled release profile.

The matrix also contains one or more lubricating agents, e.g. stearic acid, magnesium stearate, calcium stearate, waxes, polyethylene glycol, or magnesium lauryl sulfate, present in an amount of 1-3% of the total dosage form weight. A preferred embodiment comprises 0.9-1.7% stearic acid and 0.25 to 0.78% magnesium stearate.

Other excipients, such as disintegrating agents, coloring agents and flavorings may be added at the discretion of those skilled in the art.

The above components are combined to form the matrix and formed into tablets by conventional means (see Example 1). The tablets may be used as is, but are preferably coated by techniques well known in the art. An example of such a tablet coating is shown in Example 1.

The following examples describe typical batch and single tablet formulas of the controlled release dosage forms of this invention.

EXAMPLE 1

| Tablet Cores | | |
|---|---|---|
| Ingredients | Approximate g/Batch | mg/tab |
| Acetaminophen USP 90% (I) | 66,600* | 555*** |
| Pseudoephedrine Sulfate USP (II) | 7,200 | 60 |
| Dexbrompheniramine Maleate USP (III) | 369** | 3 |
| Hydroxypropyl Methylcellulose 2208 USP | 5,760 | 48 |
| Dibasic Calcium Phosphate Dihydrate USP | 11,400 | 95 |
| Stearic Acid NF | 1,200 | 10 |
| Magnesium Stearate NF | 480 | 4 |
| Purified Water USP (evaporates) | — | — |
| Alcohol 3A SD (evaporates) | — | — |
| Approximate Batch Weight (g) | 93,000 | 775 |
| Approximate Core Yield (cores) | 120,000 | |

*Equivalent to 60,000 g of Acetaminophen.
**Up to a 5% manufacturing overcharge may be added with compensating adjustments in the core weight, the amount of filler or both.
***Equivalent to 500 mg Acetaminophen.

Method of Manufacture

Blend I, II, dicalcium phosphate dihydrate and hydroxypropyl methylcellulose for 5-30 minutes in a suitable mixer. Dissolve III in hydroalcoholic mixture and use it to granulate the powder blend. Dry and mill the granulation using suitable size screen. Add remaining ingredients and blend for 3-15 minutes. Compress into suitable size tablets.

| Tablet Coating | | |
|---|---|---|
| Ingredients | Approximate g/Batch | mg/tab |
| Hydroxypropyl Methylcellulose 2910 or 2906 USP | 18,000 | 12 |
| Polyethylene glycol 3350 NF | 420 | 2.5 |
| Methylparaben NF | 20 | 0.12 |
| Propylparaben NF | 14 | 0.09 |
| Purified Water USP (evaporates) | (1) | — |
| Coloring Agent | (2) | — |

(1) Sufficient amounts of Purified Water are used as required in the coating process.
(2) An appropriate amount of a coloring agent (e.g. color dispersion solids) may be added.

Method of Manufacture

Prepare polymer solution using standard methods. Combine polymer solution with color dispersion and sufficient water. Coat tablets with colored polymer solution and polish the coated tablets using standard procedures.

EXAMPLE 2

| Tablet Cores | | |
|---|---|---|
| Ingredients | Approximate g/Batch | mg/tab |
| Acetaminophen USP | 60,000 | 500 |
| Pseudoephedrine sulfate USP | 7,200 | 60 |
| Dexbrompheniramine Maleate USP | 369* | 3 |
| Hydroxypropyl Methylcellulose 2208 USP | 6,300 | 52.5 |
| Ethylcellulose NF | 4,500 | 37.5 |
| Dibasic Calcium Phosphate Dihydrate USP | 10,080 | 84 |
| Stearic Acid NF | 1,140 | 9.5 |
| Magnesium Stearate NF | 420 | 3.5 |
| Purified Water USP (evaporates) | — | — |

-continued

| Tablet Cores | | |
|---|---|---|
| Ingredients | Approximate g/Batch | mg/tab |
| Alcohol 3A SD (evaporates) | — | — |
| Approximate Batch Weight (g) | 90,009 | 750 |
| Approximate Core Yield (cores) | 120,000 | |

*Up to a 5% manufacturing overcharge may be added with compensating adjustments in the core weight or amount of filler or both.

Method of Manufacture

Blend I, dicalcium phosphate dihydrate, II and hydroxypropyl methylcellulose in suitable mixer for 5–30 minutes. Dissolve III and ethylcellulose in 3A alcohol and use it to granulate powder blend. Dry and mill granulation using suitable size screen. Add remaining ingredients and blend for 3–15 minutes. Compress into suitable size tablets.

The tablet cores may be coated in a manner similar to that described in Example 1.

EXAMPLE 3

| Tablet Cores | | |
|---|---|---|
| Ingredients | Approximate g/Batch | mg/tab |
| Acetaminophen USP 90% | 66,600* | 555*** |
| Pseudoephedrine Sulfate USP | 7,200 | 60 |
| Dexbrompheniramine Maleate USP | 369** | 3 |
| Hydroxypropyl Methylcellulose 2910 USP | 5,760 | 48 |
| Dibasic Calcium Phosphate Dihydrate USP | 11,400 | 95 |
| Stearic acid NF | 1,200 | 10 |
| Magnesium Stearate NF | 480 | 4 |
| Purified Water USP (evaporates) | — | — |
| Alcohol 3A SD (evaporates) | — | — |
| Approximate Batch Weight (g) | 93,000 | 775 |
| Approximate Core Yield (cores) | 120,000 | |

*Equivalent to 60,000 g of Acetaminophen.
**Up to 5% manufacturing overcharge may be added with compensating adjustments in the core weight, the amount of filler, or both.
***Equivalent to 500 mg Acetaminophen

Method of Manufacture

Prepare tablets as described in Example 1. Tablets may be coated as in Example 1.

We claim:

1. A controlled release oral dosage form comprising an analgesic-effective amount of acetaminophen, an amount of pseudoephedrine or a pharmaceutically acceptable salt thereof effective in reducing nasal congestion, and an antihistaminic effective amount of dexbrompheniramine or a pharmaceutically acceptable salt thereof in a single homogeneous matrix, said matrix comprising a polymer mixture comprising hydroxypropyl methylcellulose and 1 to 45% by weight of the polymer mixture of methylcellulose, sodium carboxymethylcellulose or other cellulose ethers or combinations thereof, provided that the other cellulose ether is not ethylcellulose, wherein the polymer mixture constitutes 8–15% by weight of the uncoated doseage form.

2. A dosage form of claim 1 comprising 400 to 750 mg of acetaminophen, 15 to 75 mg of pseudoephedrine sulfate, and 1 to 5 mg of dexbrompheniramine maleate.

3. A dosage form of claim 2 comprising 500 mg acetaminophen, 60 mg pseudoephedrine sulfate and 3 mg dexbrompheniramine maleate.

4. A dosage form of claim 1 comprising 99–55% hydroxypropyl methylcellulose ethers and 1–45% by weight of the polymer mixture of methylcellulose, sodium carboxymethylcellulose or other cellulose ethers or combinations thereof, provided that the other cellulose ether is not ethylcellulose, one or more lubricants selected from stearic acid, magnesium stearate, calcium stearate, waxes, polyethylene glycol and magnesium lauryl sulfate, and one or more fillers selected from the group consisting of dibasic calcium phosphate dihydrate and lactose.

5. An oral dosage form comprising an analgesic-effective amount of acetaminophen, an amount of pseudoephedrine or a pharmaceutically acceptable salt thereof effective in reducing nasal congestion, and an antihistaminic effective amount of dexbrompheniramine or a pharmaceutically acceptable salt thereof in a single homogeneous matrix, said matrix comprising a polymer mixture comprising hydroxypropyl methylcellulose and 40 to 45% by weight of the polymer mixture of ethylcellulose, wherein the polymer mixture constitutes 8–15% by weight of the uncoated dosage form.

6. A dosage form of claim 5 wherein the polymer comprises 60–55% hydroxypropyl methylcellulose and 40–45% ethylcellulose, the total polymer weight represents 8–15% of the total dosage form weight, the total filler weight represents 10–13% of the total dosage form weight, and the total lubricant weight represents 1–3% of the total dosage form weight.

7. A dosage form of claim 6 wherein the polymer is 60–55% hydroxypropyl methylcellulose and 40–45% ethylcellulose.

8. A dosage form of claim 7 wherein the hydroxypropyl methylcellulose is hydroxypropyl methylcellulose USP 2208.

9. A dosage form of claim 6 wherein the filler is dibasic calcium phosphate dihydrate.

10. A dosage form of claim 6 wherein the lubricants are stearic acid and magnesium stearate.

11. A dosage form of claim 6 comprising 60–55% hydroxypropyl methylcellulose, 40–45% ethylcellulose, 10–13% dibasic calcium phosphate dihydrate and 1–3% of a combination of stearic acid and magnesium stearate.

12. A dosage form of claim 11 wherein the hydroxypropyl methylcellulose is hydroxypropyl methylcellulose USP 2208.

13. A dosage form of claim 12 comprising 400–750 mg acetaminophen, 15 to 75 mg pseudoephedrine sulfate and 1 to 5 mg dexbrompheniramine maleate.

14. A dosage form comprising 500 mg acetaminophen, 60 mg pseudoephedrine sulfate, 3 mg dexbrompheniramine maleate, 52.5 mg hydroxypropyl methylcellulose USP 2208, 37.5 mg ethylcellulose, 84 mg dibasic calcium phosphate dihydrate, 9.5 mg stearic acid and 3.5 mg magnesium stearate.

15. A method for effectively providing the combined effects of an analgesic, a decongestant and an antihistamine for a period of from about 8 to about 12 hours to a mammal in need of such combined effects which comprises administering to said mammal an effective amount of the dosage form defined in claim 6.

* * * * *